United States Patent [19]

Mori et al.

[11] 4,058,523

[45] Nov. 15, 1977

[54] BIS(BENZAMIDO)-BENZENE DERIVATIVES

[75] Inventors: Takashi Mori, Tama; Sakae Takaku, Ageo; Nobuhiro Oi, Hoya; Minoru Shindo, Tokyo; Takeaki Hirano, Fujimi; Shigeyuki Kataoka, Saitama; Kouji Furuno, Kokubunji, all of Japan

[73] Assignee: Chugai Seiyaku Kabushiki Kaisha, Tokyo, Japan

[21] Appl. No.: 723,444

[22] Filed: Sept. 15, 1976

Related U.S. Application Data

[63] Continuation-in-part of Ser. No. 620,216, Oct. 6, 1975, abandoned.

[30] Foreign Application Priority Data

Oct. 14, 1974 Japan .................................. 49-117123
Mar. 24, 1975 Japan .................................. 50-34510

[51] Int. Cl.² .................. C07D 295/10; C07C 103/78; A61K 31/535; A61K 31/165
[52] U.S. Cl. .............................. 544/165; 260/268 PH; 260/293.77; 260/558 A; 260/558 D; 260/558 P; 260/559 R; 260/559 A; 424/248.54; 424/250; 424/267; 424/311; 424/324; 560/138
[58] Field of Search .................. 260/247.2 A, 293.77, 260/268 R, 268 PH, 558 A, 558 P, 558 D, 559 R, 559 A, 479 R

[56] References Cited

FOREIGN PATENT DOCUMENTS 2,414,799  10/1974  Germany .............................. 260/559

OTHER PUBLICATIONS

Mori et al., CA 84:115626k (1976).

Primary Examiner—Daniel E. Wyman
Assistant Examiner—Thomas A. Waltz
Attorney, Agent, or Firm—Browdy and Neimark

[57] ABSTRACT

Bis(benzamido)-benzene derivatives having various pharmaceutical activities such as activity for preventing and treating peptic ulcer, peripheral vasodilating action, hypotensive activity and analgesic activity and represented by the formula

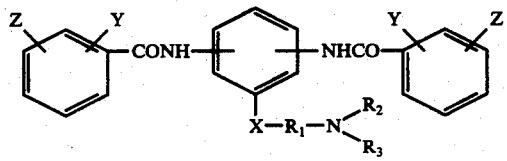

wherein X, Y, Z, $R_1$, $R_2$ and $R_3$ are as defined hereinafter and a process for preparing the same are disclosed.

54 Claims, No Drawings

BIS(BENZAMIDO)-BENZENE DERIVATIVES

CROSS REFERENCE TO RELATED APPLICATION

This application is a continuation-in-part application of copending application Ser. No. 620,216 filed on Oct. 6, 1975, now abandoned.

This invention relates to bis(benzamido)-benzene derivatives represented by the formula

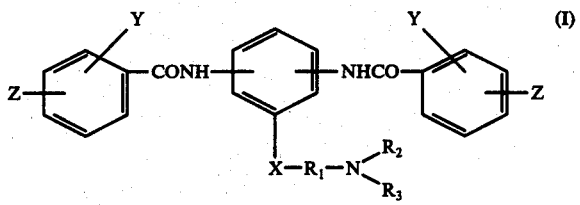

wherein X is direct bond, oxygen,

or —CONH— where the CO moiety is bonded to the phenylene group, $R_1$ is straight or branched lower alkylene, $R_2$ and $R_3$ are the same or different and each represents lower alkyl or they may be bonded to each other directly or through a hetero atom to form piperidino or morpholino, $R_4$ is lower alkyl and it may be bonded to $R_2$ or $R_3$ to form piperazino and Y and Z are same or different and each represents hydrogen, lower alkyl, hydroxy, lower alkoxy, lower alkanoyloxy or halogen, and its acid addition salt.

The object compound (I) is prepared, for example, by reacting a compound represented by the formula

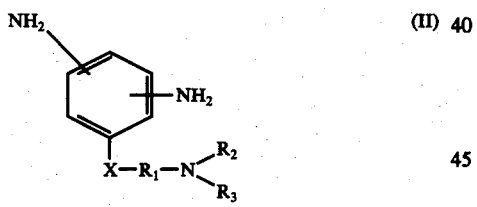

wherein X, $R_1$, $R_2$ and $R_3$ are as defined above or its functional derivative at the primary amino group with a compound represented by the formula

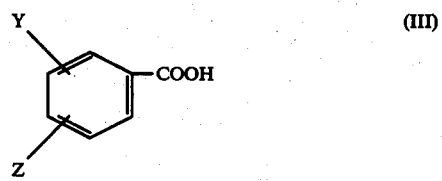

wherein Y and Z are as defined above or a functional derivative of the carboxyl group and then, if necessary, hydrolizing the ester group or alkanoylating the phenolic hydroxy group of the resulting compound.

The compound of formula I which is prepared according to this invention is novel and has various pharmacological activities such as activity for preventing and treating experimentally induced peptic ulcer in test animals, peripheral vasodilating action, hypotensive activity and analgesic activity; therefore it is very useful for medicine.

The starting compound (II) according to this invention is novel and is obtained by reducing the corresponding dinitro compound represented by the formula

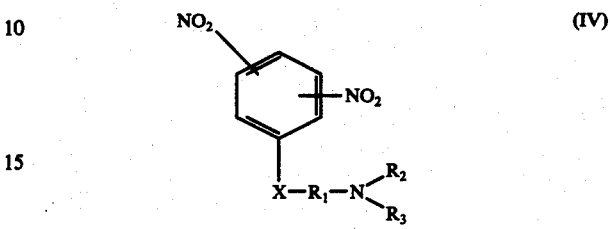

wherein $R_1$, $R_2$ and $R_3$ are as defined above, in a conventional way. The dinitro compound (IV) is prepared by, for example, the following processes.

i. In the case of X = oxygen:

A dinitrochlorobenzene represented by the formula

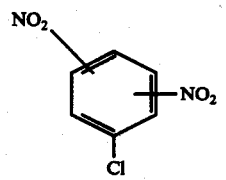

is reacted with a dialkylaminoalkanol represented by the formula

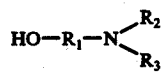

wherein $R_1$, $R_2$ and $R_3$ are as defined above to obtain the compound (IV).

ii. In the case of X = —COHN—:

A dinitrobenzoic acid chloride represented by the formula

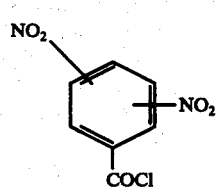

is reacted with a diamine represented by the formula

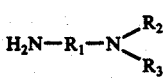

wherein $R_1$, $R_2$ and $R_3$ are as defined above to obtain the compound iii. In the case of X = direct bond:

A dinitrophenylacetic acid represented by the formula

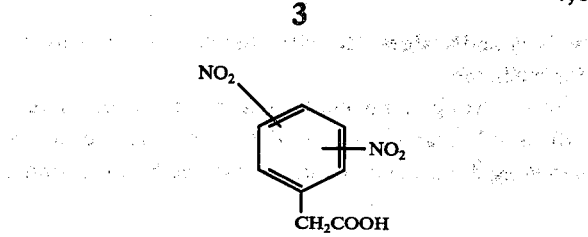

is reacted with an amine represented by the formula

wherein $R_2$ and $R_3$ are as defined above and formaldehyde to obtain the compound (IV) wherein $R_1$ is ethylene.

iv. In the case of X =

A dinitrochlorobenzene represented by the formula

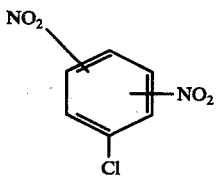

is reacted with a diamine represented by the formula

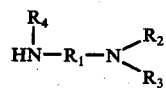

wherein $R_1$, $R_2$, $R_3$ and $R_4$ are as defined above to obtain the compound (IV).

In the practice of the process (i) the reaction of the dinitrochlorobenzene with the dialkylaminoalkanol is carried out in an inactive solvent, for example, benzene, toluene, xylene, tetrahydrofuran, dioxane, etc. at 0° − 20° C in the presence of a basic substance, for example, sodium hydride, sodium hydroxide, etc.

In the practice of the process (ii) the reaction of the dinitrobenzoic acid chloride with the diamine is carried out in a solvent, for example, tetrahydrofuran, dioxane, etc. at from 0° C to room temperature in the presence or absence of basic substance, for example, sodium carbonate, pyridine, triethylamine.

In the practice of the process (iii) the dinitrophenylacetic acid is reacted with the amine and formaldehyde in a solvent, for example, ethanol, methanol, etc. at room temperature.

In the practice of the process (iv) the reaction of the dinitrochlorobenzene with the diamine is carried out in a solvent, for example, ethanol, methanol, ethyl ether, tetrahydrofuran, dioxane, benzene, toluene etc. at from room temperature to reflux temperature of the solvent used.

In the practice of the reduction of the dinitro compound (IV) to the starting compound (II), the dinitro compound (IV) is reduced by using a catalyst, for example, Raney nickel, palladium-carbon etc. in a solvent, for example water, ethanol, methanol, tetrahydrofuran, acetic acid etc. at from room temperature to 100° C and hydrogen pressure of 1 − 50 atmospheres.

The starting compounds of formula II include dialkylaminoalkoxy-2,4-diaminobenzenes, both alkoxy and alkyl groups of which have carbon atoms of from 1 to 4, for example, 1-(2'-dimethylaminoethoxy)-2,4-diaminobenzene, 1-(2'-diethylaminoethoxy)-2,4-diaminobenzene, 1-(2'-morpholinoethoxy)-2,4-diaminobenzene, 1-(2'-dimethylamino-2',2'-dimethylethoxy)-2,4-diaminobenzene, 1-(3'-dimethylaminopropoxy)-2,4-diaminobenzene, 1-(3'-diethylaminopropoxy)-2,4-diaminobenzene and 1-(4'-dimethylaminobutoxy)-2,4-diaminobenzene; [N-(dialkylaminoalkyl)-carbamoyl]-diaminobenzenes both alkyl groups of which have carbon atoms of from 1 to 4, for example, 1-[N-(2'-diethylaminoethyl)-carbamoyl]-2,4-diaminobenzene, 1-[N-(2'-diethylaminoethyl)-carbamoyl]-2,5-diaminobenzene, 1-[N-(2'-diethylaminoethyl)-carbamoyl]-3,5-diaminobenzene, 1-[N-(3'-dimethylaminopropyl)-carbamoyl]-2,4-diaminobenzene, and 1-[N-(3'-diethylaminopropyl)-carbamoyl]-2,4-diaminobenzene; dialkylaminoalkyldiaminobenzenes both alkyl groups of which have carbon atoms of from 1 to 4, for example, 1-(2'-dimethylaminoethyl)-2,4-diaminobenzene, and 1-(2'-diethylaminoethyl)-2,4-diaminobenzene; and 1-[2'-(N-morpholino)-ethyl ]-2,4-diaminobenzene; 1-[2'-(N-piperidino)-ethyl]-2,4-diaminobenzene; 1-[N-methyl-(N'-piperidino)]-2,4-diaminobenzene; 1-[N-(2'-dimethylaminoethyl)-N-methylamino]-2,4-diaminobenzene and the like. The compound (II) may be used in a process according to this invention as an acid addition salt thereof, such as the hydrochloride. Compounds the amino group of which is activated with phosphorous trichloride, an ester of chlorophosphorous acid or the like may be also used as a starting compound.

The starting compounds representative of formula (III) include benzoic acid; alkyl substituted benzoic acid the alkyl group of which have carbon atoms of from 1 to 4, for example, 2-methylbenzoic acid, 3-methylbenzoic acid and 4-methylbenzoic acid; alkoxybenzoic acids the alkoxy group(s) of which have carbon atoms of from 1 to 4, for example, 2-methoxybenzoic acid, 4-methoxybenzoic acid and 2-ethoxybenzoic acid; alkanoyloxybenzoic acids the alkanoyl group(s) of which have carbon atoms of from 2 to 4, for example, 2-acetoxybenzoic acid; halobenzoic acids, for example, 2-chlorobenzoic acid; 2-hydroxybenzoic acid; 2-methoxy-4-methylbenzoic acid; 2,3-dimethoxy benzoic acid and the like.

Among the functional derivatives of the compounds (III) are included, for example, acid halides, esters, anhydrides of the benzoic acids or the benzoic acid with another acid such as carbonic acid, sulfuric acid, phosphoric acid or sulfonic acid and the like.

The reaction of this invention is carried out by condensing the compound of formula (II) with a reactive derivative of the compound represented by the formula (III) at a temperature of from usually −10° to 100° C, preferably 0° to 50° C for 0.5–4 hours. A solvent which is used for this reaction is, for example, water, benzene, toluene, tetrahydrofuran, diethylether, dioxane, dimethylformamide, chloroform, methylene chloride, acetonitrile, acetone, carbon tetrachloride, ethyl acetate or the like. Accelerators for the condensation reaction of this invention include, for example, inorganic bases such as hydroxides, acetates and carbonates of an alkali metal or alkaline earth metal, for example, potassium acetate, sodium acetate, sodium carbonate, potassium carbonate, sodium hydroxide, calcium acetate and calcium carbonate; and tertiary amine organic bases, for example, pyridine, triethylamine, dimethylaniline and picoline.

A compound of formula (II) the amino group of which was activated with phosphorous trichloride, ethyl chlorophosphite or methyl chlorophosphite or the like may be reacted with a compound of formula (III) at a temperature of from room temperature to reflux temperature of the solvent used for 0.5–3 hours. In case Y and/or Z of formula (III) are hydroxy groups, it is preferable to carry out this reaction after protecting them. This reaction is carried out in neutral solvent such as benzene, toluene, xylene, dioxane or tetrahydrofuran or in a basic solvent such as pyridine, triethylamine, dimethylaniline or picoline. When the reaction is carried out in a neutral solvent, the use of tertiary amine is preferred.

Furthermore, a compound of formula (II) can be reacted with a compound of formula (III) in an inert solvent at a temperature of from room temperature to reflux temperature of the solvent used for 1–5 hours in the presence of an amide formation accelerator such as imide compound, e.g., N,N'-dicyclohexylcarbodiimide, N-cyclohexyl-N'-morpholinoethylcarbodiimide or N,N'-diethylcarbodiimide; imine compound e.g., diphenylketene-N-cyclohexylimine or pentamethyleneketene-N-cyclohexylimine; or an ester of phosphoric or phosphorous acid e.g., triethyl phosphite, ethyl polyphosphate or isopropyl polyphosphate. In case the compound of formula (II) has hydroxyl radical(s), it is preferable to protect the radical(s) prior to the reaction. Inert solvents which may be used in this reaction include, for example, benzene, toluene, tetrahydrofuran, chloroform, dioxane, acetonitrile, dimethylformamide and the like.

Thus, the compound of formula (I) may be obtained as a free base or an acid addition salt. The compound may be hydrolized in case it is in the form of ester, or may be acylated to introduce a lower acyl group therein when the compound has phenolic hydroxyl(s). These reactions can be carried out in any conventional manner. For example, the hydrolysis of the ester can be accomplished by the action of a hydroxide or carbonate of alkali metal or alkaline earth metal in water or of aqueous ammonia at a temperature of from room temperature to 100° C for 0.5–30 hours. The acylation of the phenolic hydroxyl radical can be carried out by the action of an acid chloride or an acid anhydride of a lower fatty acid at 0° – 100° C for 1–10 hours. The use of solvent is not essential, but an inert solvent such as tetrahydrofuran, dioxane, acetone or chloroform may be used.

This invention is further illustrated by the following Experiments and Examples, but they are not to be construed as limiting the scope of this invention.

EXPERIMENT 1

Protective Action on pylorus ligature ulcer formation

The pylorus of Sprague-Dawley strain male rats weighing 150–200 g that had abstained from food, but not water for 48 hours was ligatured under ether anethsia. Each rat was allowed to stand individually in a cage for 16 hours without food and water. At the end of this term, the rats were sacrificed by an overdose of diethyl ether. The stomach was taken out of each animal and the gastric mucosa was observed by the use of a dissecting microscope.

Ulcers observed in the gastric mucosa were evaluated on a scale of from 0 to 5 defined as follows.

0: No lesion was observed.
1: Hemorrhage and/or erosion were observed.
2: One to five small ulcers less than 3 mm in diameter were observed.
3: Six or more small ulcers and/or a large ulcer more than 3 mm in diameter were observed.
4: Two or more large ulcers were observed.
5: At least one perforating ulcer was observed.

A test compound was administered as an aqueous solution in an equivalent molar of hydrochloric acid in the duodenum immediately after the pylorus ligature.

The results are shown in Table I.

Table I

| Protective action on pylorus ligature ulcer formation | | | | | |
|---|---|---|---|---|---|
| Test Compound | Dose (mg/kg) | Number of Animals | Death Rate | Precent Perforating Ulcers | Ulcer Index (mean value ± standard deviation) | Percent Inhibition |
| Control | — | 9 | 47 | 56 | 4.0 ± 1.3 | — |
| 1-(3'-dimethylaminopropoxy)-2,4-bis(2"-methylbenz-amido)-benzene | 50 | 5 | 20 | 20 | 3.2 ± 1.3 | 20 |
| | 100 | 5 | 0 | 0 | 2.6 ± 0.5* | 35 |
| | 200 | 5 | 0 | 0 | 0*** | 100 |
| 1-(3'-dimethylaminopropoxy)-2,4-bis(3"-methylbenz-amido)-benzene | 50 | 6 | 33 | 50 | 4.0 ± 1.1 | 0 |
| | 100 | 6 | 0 | 0 | 2.0 ± 1.4* | 50 |
| | 200 | 6 | 0 | 0 | 1.0 + 1.1*** | 75 |
| 1-[N-(3'-dimethylaminopropyl)-carbamoyl]-2,4-bis(2"-methylbenzamido)-benzene | 200 | 7 | 0 | 0 | 1.4 ± 1.4** | 65 |
| 1-[N-(3'-dimethylaminopropyl)-carbamoyl]-2,4-bis(3"-methylbenzamido)-benzene | 200 | 6 | 0 | 0 | 2.5 ± 1.4* | 38 |

*$P<0.05$
**$P<0.01$
***$P<0.001$

EXPERIMENT 2

Action on stress-induced ulcer formation

Sprague-Dawley strain male rats weighing 200–250 g were deprived of food for 24 hours, and then laid down on their backs on a screen and fixed by fastening their limbs with a strand. The fixed rats were submerged in water bath to the depth of ensiform process with their hind legs dipped first. Sixteen hours after the submergence, the rats were brought out from the bath and their stomachs were taken out. After light fixation with a 1% formalin aqueous solution, the stomach of each animal was cut open along their greater curvature and gastric mucosa was observed through a dissecting microscope.

The ulcer was evaluated on an ulcer index calculated from the following equation:

Ulcer Index = $a + b/10$ wherein $a$ is the number of big ulcers more than 3 mm in diameter and $b$ is the number of small ulcers up to 3 mm in diameter.

A test compound was orally administered as a suspension in a 1% gum arabic aqueous solution, 10 minutes before exposure to stress.

The results are shown in Table II below.

Table II

Inhibitory action on a stress-induced ulcer formation

| Test Compound | Dose (mg/kg) | Number of Animals | Number of Ulcers/Stomach up to 3 mm | 3 mm or larger | Ulcer Index (mean value ± standard deviation) | Percent Inhibition |
|---|---|---|---|---|---|---|
| Control | — | 10 | 46 | 1.3 | 6.1 ± 2.3 | — |
| 1-(3'-dimethylamino-propoxy)-2,4-bis(2''-methylbenzamido)-benzene | 30 | 5 | 23 | 0.6 | 2.8 ± 0.8** | 54 |
|  | 45 | 6 | 17 | 0.2 | 2.0 ± 0.6*** | 67 |
|  | 67 | 6 | 9 | 0.2 | 1.0 ± 0.9*** | 84 |
|  | 100 | 5 | 4 | 0 | 0.4 ± 0.5*** | 93 |
| 1-(3'-dimethylamino-propoxy)-2,4-bis(3''-methylbenzamido)-benzene | 30 | 5 | 21 | 0.5 | 2.6 ± 2.1* | 57 |
|  | 45 | 6 | 9 | 1.0 | 2.0 ± 1.7** | 67 |
|  | 67 | 6 | 7 | 0.8 | 1.5 ± 2.7** | 75 |
|  | 100 | 5 | 11 | 0.8 | 2.0 ± 2.1** | 67 |
| 1-[N-(3'-dimethylamino-propyl)-carbamoyl]-2,4-bis(2''-methylbenzamido)-benzene | 100 | 5 | 23 | 0.8 | 3.0 ± 1.0* | 51 |
| 1-[N-(3'-dimethylamino-propyl)-carbamoyl]-2,4-bis(3''-methylbenzamido)-benzene | 100 | 5 | 17 | 0.6 | 2.4 ± 2.1** | 61 |
| 1-(3'-dimethylamino-propoxy)-2,4-bis(2''-methoxybenzamido)-benzene | 100 | 4 | 13 | 0.5 | 1.8 ± 2.4* | 71 |
| 1-(3'-diethylamino-propoxy)-2,4-bis(4''-methylbenzamido)-benzene | 100 | 4 | 17 | 1.3 | 3.0 ± 0.8* | 52 |
| 1-(4'-diethylamino-butoxy)-2,4-bis(2''-methoxybenzamido)-benzene | 100 | 4 | 11 | 0.8 | 1.8 ± 1.5* | 71 |
| 1-(3'-diethylamino-propoxy)-2,4-bis(2''-methoxybenzamido)-benzene | 100 | 4 | 8 | 0.8 | 1.5 ± 2.4* | 76 |
| 1-(3'-diethylamino-propoxy)-2,4-bis(2''-methylbenzamido)-benzene | 100 | 4 | 6 | 0 | 0.5 ± 1.0** | 92 |
| 1-(3'-diethylamino-propoxy)-2,4-bis(3''-methylbenzamido)-benzene | 100 | 4 | 6 | 0.3 | 0.8 ± 1.0** | 87 |
| 1-(4'-dimethylamino-butoxy)-2,4-bis(2''-methylbenzamido)-benzene | 100 | 6 | 6 | 0.2 | 1.0 ± 0.6** | 85 |
| 1-(4'-dimethylamino-butoxy)-2,4-bis(3''-methylbenzamido)-benzene | 100 | 6 | 8 | 0.5 | 1.2 ± 1.6** | 82 |
| 1-[N-(2'-diethylamino-ethyl)-carbamoyl]-2,4-bis(2''-methoxybenzamido)-benzene | 100 | 4 | 12 | 1.1 | 3.8 ± 2.3 | 40 |
| 1-[N-(3'-diethylamino-propyl)-carbamoyl]-2,4-bis(2''-methoxybenzamido)-benzene | 100 | 4 | 11 | 0 | 1.3 ± 0.5** | 80 |
| 1-[N-(2'-diethylamino-ethyl)-carbamoyl]-2,4-bis(2''-methylbenzamido)-benzene | 100 | 6 | 29 | 1.2 | 4.2 ± 0.4 | 38 |
| 1-[N-(2'-diethylamino-ethyl)-carbamoyl]-2,4-bis(3''-methylbenzamido)-benzene | 100 | 4 | 27 | 1.3 | 4.0 ± 2.6 | 46 |
| 1-[N-(2'-diethylamino-ethyl)-carbamoyl]-2,4-bis(4''-methylbenzamido)-benzene | 100 | 5 | 26 | 1.4 | 4.0 ± 1.4 | 40 |
| 1-[N-(2'-diethylamino-ethyl)-carbamoyl]-3,5-bis(2''-methoxy-benzamido)-benzene | 100 | 4 | 13 | 3.0 | 4.3 ± 2.2 | 33 |
| 1-[N-(3'-diethylamino-propyl)-carbamoyl]-2,4-bis(3''-methyl-benzamido)-benzene | 100 | 6 | 12 | 0 | 1.0 ± 0.6** | 85 |
| 1-[N-(3'-dimethylamino-propyl)-carbamoyl]-2,4-bis(4''-methyl-benzamido)-benzene | 100 | 6 | 19 | 1.0 | 3.0 ± 1.4** | 60 |

*P<0.05
**P<0.01
***P<0.001

EXPERIMENT 3

1. Acute toxicity

Acute toxicity of 1-(3'-dimethylaminopropoxy)-2,4-bis(2"-methylbenzamido)-benzene, 1-(3'-dimethylaminopropoxy)-2,4-bis(3"-methylbenzamido)-benzene, 1-[N-(3-dimethylaminopropyl)-carbamoyl]-2,4-bis(2"-methylbenzamido)-benzene and 1-[N-(3'-dimethylaminopropyl)-carbamoyl]-2,4-bis(3"-methylbenzamido)-benzene were observed by the use of ddY strain male mice (5 weeks old) which were administered orally or intravenously with one of the compounds.

In the case of intravenous administration, the hydrochloride of test compound was dissolved in a physiological saline solution and administered by injecting into a vein of the tail. $LD_{50}$ was determined by the "Up and Down" method.

When the administration was effected orally, the test compound was suspended in a 1% gum arabic aqueous solution and the suspension was administered orally by gavage. $LD_{50}$ was determined by the Litchfield and Wilcoxon method or Miller and Tainter method based on death rate of each group of rats 10 days after the administration of the compound.

Table III
Acute toxicity in mice

| Test compound | Administration Route | $LD_{50}$ (mg/kg) |
|---|---|---|
| 1-(3'-dimethylamino-propoxy)-2,4-bis(2"-methylbenzamido)-benzene | i.v.* oral | 42 a) 2520 b) |
| 1-(3'-dimethylamino-propoxy)-2,4-bis(3"-methylbenzamido)-benzene | i.v. oral | 38 a) 4700 b) |
| 1-[N-(3'-dimethylamino-propyl)-carbamoyl]-2,4-bis(2"-methylbenzamido)-benzene | i.v. oral | 111 a) >11000 |
| 1-[N-(3'-dimethylamino-propyl)-carbamoyl]-2,4-bis(3"-methylbenzamido)-benzene | i.v. oral | 88 a) 5100 c) |

*intravanous
a) Up and Down Method
b) Litchfield and Wilcoxon Method
c) Miller and Tainter Method

EXAMPLE 1

To a mixture of potassium carbonate (25 g), water (50 ml) and tetrahydrofuran (130 ml) was added 1-(3'-diethylaminopropoxy)-2,4-diaminobenzene trihydrochloride (10.4 g) with stirring while cooling with ice. Immediately after the addition, 2-methylbenzoyl chloride (14 g) was further added to the mixture at a time and the resulting mixture was stirred at room temperature for 5 hours. After the completion of the reaction, the reaction mixture was extracted with benzene and the extract was washed with water and basic substances were transferred from the organic layer to an aqueous layer with the use of a diluted hydrochloric aqueous solution. When the hydrochloric acid addition salts of the basic substances were hardly soluble, a small amount of methanol was used to dissolve them. The aqueous layer was washed with benzene and the pH adjusted to 9–10 with potassium carbonate and extracted with benzene. The organic layer was washed with water, dried over potassium carbonate and condensed. The residue was purified by passing it through a column chromatography with silica gel by eluting with benzene-methanol, and recrystallized from benzene-hexane to obtain 9.9 g of 1-(3'-diethylaminopropoxy)-2,4-bis(2"-methylbenzamido)-benzene having a melting point between 99° – 100° C.

Analysis: Calcd. for $C_{29}H_{35}N_3O_3$: C, 73.5; H, 7.5; N, 8.9 (%) Found: C, 73.3; H, 7.6; N, 8.9 (%).

EXAMPLE 2

By a procedure similar to that described in Example 1, 1-(3'-diethylaminopropoxy)-2,4-diaminobenzene trihydrochloride was subjected to condensation reaction with 3-methylbenzoylchloride to obtain 1-(3'-diethylaminopropoxy)-2,4-bis(3"-methylbenzamido)-benzene having a melting point between 113° and 114° C. (Yield: 72%)

Analysis: Calcd. for $C_{29}H_{35}N_3O_3$: C, 73.5, H, 7.5; N, 8.9 (%) Found: C, 73.7; H, 7.4; N, 9.0 (%).

EXAMPLE 3

To a mixture of potassium carbonate (29 g), water (110 ml) and dioxane (110 ml) was added 1-[N-(2'-diethylaminoethyl)-carbamoyl]-2,4-diaminobenzene trihydrochloride and to the mixture was added dropwise a solution of 2-methylbenzoylchloride (16.8 g) in dioxane (20 ml) over 1 hour while stirring at room temperature in an atmosphere of nitrogen. After stirring for a further 1.5 hours, the reaction mixture was extracted with benzene, and the basic substances were transferred from the benzene layer to an aqueous layer with the use of a diluted hydrochloric acid aqueous solution. When the hydrochloric acid addition salts of the substances were hardly soluble, a small amount of methanol was used to dissolve them. After washing the aqueous solution with benzene, its pH was adjusted to 9 – 10 and extracted with benzene. The benzene layer was dried over potassium carbonate and condensed to dryness. The residue was purified by a silica gel column chromatography with chloroform-methanol as the eluent and recrystallized from benzene-ether to obtain 14 g of 1-[N-(2'-diethylaminoethyl)-carbamoyl]-2,4-bis(2"-methylbenzamido)-benzene having a melting point between 157° – 158° C.

Analysis: Calcd. for $C_{29}H_{34}N_4O_3$: C, 71.6; H, 7.0; N, 11.5 (%) Found: C, 71.8; H, 7.1; N, 11.6 (%).

EXAMPLE 4

By a procedure similar to that described in Example 1 excepting that dioxane was used instead of tetrahydrofuran, 1-(3'-diethylaminopropoxy)-2,4-diaminobenzene trihydrochloride and 4-methylbenzoylchloride were condensed. The reaction mixture was diluted with ten times as much water as the original volume, and the precipitated crystals were filtered off and washed with water. Recrystallization of the crystals from ethanol yielded 1-(3'-diethylaminopropoxy)-2,4-bis(4"-methylbenzamido)-benzene having a melting point between 148° and 149° C. (Yield: 81%)

Analysis: Calcd. for $C_{29}H_{35}N_3O_3$: C, 73.5; H, 7.5; N, 8.9 (%) Found: C, 73.6; H, 7.4; N, 9.0 (%).

EXAMPLE 5

To a mixture of potassium carbonate (6.2 g), sodium acetate trihydrate (19 g), water (100 ml) and dioxane (100 ml) was added 1-(3'-diethylaminopropoxy)-2,4-diaminobenzene trihydrochloride (10.4 g) immediately followed by adding benzoyl chloride (13 g) while cooling with ice, and thereafter, the resulting mixture was stirred at room temperature for 2 hours. Then, after the addition of water (500 ml), the pH of the mixture was adjusted to 9 – 10 and the precipitated crystals were recovered by filtration. After washing the crystals with water, they were recrystallized twice from methanol-water to obtain 7.9 g of 1-(3'-diethylaminopropoxy)-2,4-bis(benzamido)-benzene having a melting point between 139° and 140° C.

Analysis: Calcd. for $C_{27}H_{31}N_3O_3$: C, 72.8; H, 7.0; N, 9.4 (%) Found: C, 72.5; H, 7.1; N, 9.5 (%).

EXAMPLE 6

By a procedure similar to that described in Example 1, 1-(3'-dimethylaminopropoxy)-2,4-diaminobenzene trihydrochloride was condensed with 2-methylbenzoylchloride and the reaction product was treated in a manner as described in Example 1. Recrystallization from benzene-diethylether gave 1-(3'-dimethylaminopropoxy)-2,4-bis(2''-methylbenzamido)-benzene having a melting point of between 136° and 137° C. (Yield: 73%)

Analysis: Calcd. for $C_{27}H_{31}N_3O_3$: C, 72.8; H, 7.0; N, 9.4 (%) Found: C, 73.1; H, 7.0; N, 9.5 (%).

EXAMPLE 7

By a procedure similar to that described in Example 1, 1-(3'-dimethylaminopropoxy)-2,4-diaminobenzene was subjected to condensation reaction with 3-methylbenzoylchloride to obtain 1-(3'-dimethylaminopropoxy)-2,4-bis(3''-methylbenzamido)-benzene having a melting point between 120° and 121° C. (Yield: 75%)

Analysis: Calcd. for $C_{27}H_{31}N_3O_3$: C, 72.8; H, 7.0; N, 9.4 (%) Found: C, 72.8; H, 7.2; N, 9.3 (%).

EXAMPLE 8

By a procedure similar to that described in Example 1, 1-(3'-dimethylaminopropoxy)-2,4-diaminobenzene was subjected to condensation reaction with 4-methylbenzoylchloride followed by treating the reaction product in a manner similar to that described in Example 1. Recrystallization of the resulting crystals from methanol gave 1-(3'-dimethylaminopropoxy)-2,4-bis(4''-methylbenzamido)-benzene having a melting point between 163° – 164° C. (Yield: 68%)

Analysis: Calcd. for $C_{27}H_{31}N_3O_3$: C, 72.8; H, 7.0; N, 9.4 (%) Found: C, 72.5; H, 7.1; N, 9.5 (%).

EXAMPLE 9

By a procedure similar to that described in Example 1, 1-(3'-diethylaminopropoxy)-2,4-diaminobenzene trihydrochloride was subjected to condensation reaction with 2-methoxy-4-methylbenzoylchloride. The reaction product was treated in a manner similar to that described in Example 1 and recrystallized from methanol to obtain 1-(3'-diethylaminopropoxy)-2,4-bis(2''-methoxy-4''-methylbenzamido)-benzene having a melting point between 127° – 129° C (decomposition). (Yield: 65%)

Analysis: Calcd. for $C_{31}H_{39}N_3O_5$: C, 69.8; H, 7.4; N, 7.9 (%) Found: C, 69.7; H, 7.6; N, 8.1 (%).

EXAMPLE 10

By a procedure similar to that described in Example 1, 1-(3'-dimethylaminopropoxy)-2,4-diaminobenzene trihydrochloride was subjected to condensation reaction with 2,3-dimethoxybenzoylchloride. The reaction mixture was extracted with benzene, the organic layer was washed with water and gaseous hydrogen chloride was bubbled into the layer to precipitate crystals as hydrochloric acid addition salt. The crystals which were recovered by filtration were dissolved in methanol-water and returned to free base by the addition of a potassium carbonate aqueous solution and extracted with benzene. The benzene layer was washed with water and dried, and condensed to dryness. Recrystallization of the residue from ethanol gave 1-(3'-dimethylaminopropoxy)-2,4-bis(2'',3''-dimethoxybenzamido)-benzene having a melting point between 131° – 132° C. (Yield: 64%)

Analysis: Calcd. for $C_{29}H_{35}N_3O_7$: C, 64.8; H, 6.6; N, 7.8 (%) Found: C, 64.6; H, 6.8; N, 7.7 (%).

EXAMPLE 11

By a procedure similar to that described in Example 1, 1-(3'-diethylaminopropoxy)-2,4-diaminobenzene trihydrochloride was subjected to condensation reaction with 2-chlorobenzoylchloride. The reaction mixture was extracted with benzene and, after the benzene layer was washed with water and dried, gaseous hydrochloride was bubbled into the layer to precipitate crystals as hydrochloric acid addition salt. After recrystallization of the crystals from ethanol, they were dissolved in water. The pH of the solution was adjusted to 9 – 10 by the use of potassium carbonate and the solution was extracted with benzene. The benzene layer was washed with water, dried and condensed to dryness. The residue was recrystallized from benzenediethylether-hexane to obtain 1-(3'-diethylaminopropoxy)-2,4-bis(2''-chlorobenzamido)-benzene having a melting point between 82° – 83° C. (Yield: 70%)

Analysis: Calcd. for $C_{27}H_{29}N_3O_3Cl_2$: C, 63.0; H, 5.7; N, 8.2 (%) Found: C, 63.1; H, 5.9; N, 8.1 (%).

EXAMPLE 12

By a procedure similar to that described in Example 1 excepting that dioxane was used instead of tetrahydrofuran, 1-(3'-diethylaminopropoxy)-2,4-diaminobenzene trihydrochloride was subjected to condensation reaction with 4-methoxybenzoylchloride and the reaction mixture was diluted with ten times as much water as the original volume to precipitate crystals. After recovering the crystals by filtration, they were washed with water and recrystallized from ethanol to obtain 1-(3'-diethylaminopropoxy)-2,4-bis(4''-methoxybenzamido)-benzene having a melting point between 149° – 150° C. (Yield: 80%)

Analysis: Calcd. for $C_{29}H_{35}N_3O_5$: C, 68.9; H, 7.0; N, 8.3 (%) Found: C, 68.8; H, 7.0; N, 8.3 (%).

EXAMPLE 13

A mixture of potassium carbonate (35 g), water (50 ml), tetrahydrofuran (150 ml) and 1-[N-(3'-diethylaminopropyl)-carbamoyl]-2,4-diaminobenzene trihydrochloride (11 g) was added dropwise to 2-methylbenzoylchloride (35 g) over 30 minutes while stirring in nitrogen atmosphere and heating at reflux followed by stirring under the same conditions for 3 hours. The reaction mixture was treated in a manner similar to that of Example 3 to obtain 1-[N-(3'-diethylaminopropyl)-carbamoyl]-2,4-bis(2''-methylbenzamido)-benzene having a melting point between 138° – 140° C. (Yield: 65%)

Analysis: Calcd. for $C_{30}H_{36}N_4O_3$: C, 72.0; H, 7.3; N, 11.2 (%) Found: C, 71.9; H, 7.2; N, 11.5 (%).

EXAMPLE 14

By a procedure similar to that described in Example 1, 1-(4'-dimethylaminobutoxy)-2,4-diaminobenzene trihydrochloride and 2-methylbenzoylchloride were subjected to condensation reaction and the reaction mixture was treated in a manner similar to that of Example 3 to obtain 1-(4'-dimethylaminobutoxy)-2,4-bis(2''-methylbenzamido)-benzene having a melting point between 142°–144°. (Yield: 80%)

Analysis: Calcd. for $C_{28}H_{33}N_3O_3$: C, 73.2; H, 7.2; N, 9.1 (%) Found: C, 73.5; H, 7.4; N, 9.2 (%).

EXAMPLE 15

By a procedure similar to that described in Example 14, 1-(4'-dimethylaminobutoxy)-2,4-diaminobenzene trihydrochloride and 3-methylbenzoylchloride were subjected to condensation reaction and the reaction mixture was treated in a manner similar to that of Example 14 to obtain 1-(4'-dimethylaminobutoxy)-2,4-bis(3''-methylbenzamido)-benzene having a melting point between 105°–107° C. (Yield: 79%)

Analysis: Calcd. for $C_{28}H_{33}N_3O_3$: C, 73.2; H, 7.2; N, 9.1 (%) Found: C, 73.1; H, 7.3; N, 9.2 (%).

EXAMPLE 16

By a procedure similar to that described in Example 3, 1-[N-(2'-diethylaminoethyl)-carbamoyl]-2,4-diaminobenzene and 3-methylbenzoylchloride were subjected to condensation reaction. The reaction mixture was treated in a manner similar to that of Example 3 to obtain 1-[N-(2'-diethylaminoethyl)-carbamoyl]-2,4-bis(3''-methylbenzamido)-benzene having a melting point between 167°–168° C. (Yield: 67%)

Analysis: Calcd. for $C_{29}H_{34}N_4O_3$: C, 71.6; H, 7.0; N, 11.5 (%) Found: C, 71.8; H, 7.2; N, 11.7 (%).

EXAMPLE 17

By a procedure similar to that described in Example 6, 1-[2'-(N-morpholino)-ethoxy]-2,4-diaminobenzene and 2-methylbenzoylchloride were subjected to condensation reaction. The reaction mixture was treated in a manner similar to that of Example 6 to obtain 1-[2'-(N-morpholino)ethoxy]-2,4-bis(2''-methylbenzamido)-benzene having a melting point between 80°–81° C. (Yield: 60%)

Analysis: Calcd. for $C_{28}H_{31}N_3O_4$: C, 71.0; H, 6.6; N, 8.9 (%) Found: C, 71.1; H, 6.8; N, 9.0 (%).

EXAMPLE 18

By a procedure similar to that described in Example 13, 1-[N-(3'-diethylaminopropyl)-carbamoyl]-2,4-diaminobenzene and 3-methylbenzoylchloride were subjected to condensation reaction. The reaction mixture was treated in a manner similar to that of Example 13 to obtain 1-[N(3'-diethylaminopropyl)-carbamoyl]-2,4-bis(3''-methylbenzamido)-benzene having a melting point between 138°–139° C. (Yield: 66%)

Analysis: Calcd. for $C_{30}H_{36}N_4O_3$: C, 72.0; H, 7.3; N, 11.2 (%) Found: C, 71.8; H, 7.2; N, 11.3 (%).

EXAMPLE 19

By a procedure similar to that described in Example 3, 1-[N-(2'-diethylaminoethyl)-carbamoyl]-2,4-diaminobenzene trihydrochloride and 4-methylbenzoylchloride were subjected to condensation reaction and the reaction mixture was treated in a manner similar to that in Example 3 to obtain 1-[N-(2'-diethylaminoethyl)-carbamoyl]-2,4-bis(4''-methylbenzamido)-benzene having a melting point between 178°–179° C. (Yield: 64%)

Analysis: Calcd. for $C_{29}H_{34}N_4O_3$: C, 71.6; H, 7.0; N, 11.5 (%) Found: C, 71.5; H, 7.2; N, 11.6 (%).

EXAMPLE 20

By a procedure similar to that described in Example 1, 1-(3'-dimethylminopropoxy)-2,4-diaminobenzene trihydrochloride and 4-methoxybenzoylchloride were subjected to condensation reaction. After completion of the reaction, the reaction mixture was extracted with benzene and the benzene layer was washed with water and dried over potassium carbonate and decolorized with silica gel. Gaseous hydrogen chloride was bubbled into the benzene and precipitated hydrochloride was recovered by filtration. The hydrochloride was washed with ethanol-acetone, dissolved in an aqueous methanol, converted to free base by adding an aqueous solution of potassium carbonate and extracted with benzene. The benzene layer was washed with water, dried, and concentrated to dryness. The residue was recrystallized from ethanol to obtain 1-(3'-dimethylaminopropoxy)-2,4-bis(4''-methoxybenzamido)-benzene having a melting point between 171°–172° C. (Yield: 62%)

Analysis: Calcd. for $C_{27}H_{31}N_3O_5$: C, 67.9; H, 6.5; N, 8.8 (%) Found: C, 68.0; H, 6.6; N, 8.6 (%).

EXAMPLE 21

Potassium carbonate (17 g) was dissolved in water (40 ml) and to the solution was added dioxane (90 ml). To the mixture was added 1-(2'-diethylaminoethoxy)-2,4-diaminobenzene trihydrochloride (6.6 g) and 2-ethoxybenzoylchloride (11g) at a temperature of from 5° to 10° C and then the resulting mixture was stirred at room temperature for 1 hour. Then, water (500 ml) was added to the mixture and undissolved materials were recovered, washed with water and dissolved in acetone. Gaseous hydrogen chloride was bubbled through the solution and diethyl ether was added to precipitate hydrochloride. The hydrochloride was recovered and recrystallized from ethanol to obtain 6.8 g of 1-(2'-diethylaminoethoxy)-2,4-bis(2''-ethoxybenzamido)-benzene hydrochloride having a melting point between 194°–195° C.

Analysis: Calcd. for $C_{30}H_{38}N_3O_5Cl$: C, 64.8; H, 6.9; N, 7.6 (%) Found: C, 64.7; H, 6.9; N, 7.7 (%).

EXAMPLE 22

Potassium carbonate (4.2 g) and sodium acetate trihydrate (13 g) were dissolved in water (80 ml) followed by adding dioxane (80 ml). To the mixture was added 1-(2'-diethylaminoethoxy)-2,4-diaminobenzene trihydrochloride (6.6 g) at a temperature between 5°–10° C, and then 2-acetoxybenzoylchloride (12 g) followed by stirring at that temperature for 1 hour. After cooling to room temperature, concentrated aqueous ammonia (30 ml) was added to the mixture which was allowed to stand at room temperature for 30 minutes. After the addition of water (500 ml), the pH of the mixture was adjusted to 8 and the precipitated crystals were recovered by filtration, washed with water and dried. The crystals were dissolved in methanol saturated with gaseous hydrogen chloride and the solution was concentrated to dryness. After recrystallization of the residue from ethanol the yield was 5.9 g of 1-(2'- diethylaminoethoxy)-2,4-bis(2''-hydroxybenzamido)-benzene hydrochloride having a melting point between 216°–217° C.

Analysis: Calcd. for $C_{26}H_{30}N_3O_5Cl$: C, 62.5; H, 6.0; N, 8.4 (%) Found: C, 62.4; H, 6.1; N, 8.3 (%).

EXAMPLE 23

To a mixture of potassium carbonate (2.8 g), sodium acetate (2.5 g), water (30 ml) and dioxane (40 ml) was added N-(2,4-diaminophenyl)-N'-methylpiperazine trihydrochloride (3.5 g) and then 2-acetoxybenzoylchloride (6 g) at a temperature of from 5° to 10° C followed by stirring at that temperature for 1 hour. After the addition of concentrated aqueous ammonia (20 ml), the mixture was allowed to stand at room temperature for 30 minutes followed by adding water (300 ml). The pH of the mixture was adjusted to 8 with duluted hydrochloric acid to precipitate crystals. The crystals were washed with water, dried and dissolved in methanol saturated with gaseous hydrogen chloride. The solution was concentrated to dryness and the residue was recrystallized from methanol-water to obtain 2.9 g of N-[2,4-bis(2'-hydroxybenzamido)-phenyl]-N'-methylpiperazine hydrochloride having a melting point between 290°–294° C (decomposition).

Analysis: Calcd. for $C_{25}H_{27}N_4O_4Cl$: C, 62.2; H, 5.6; N, 11.6 (%) Found: C, 62.2; H, 5.7; N, 11.7 (%).

EXAMPLE 24

To a mixture of potassium carbonate (120 g), water (300 ml), dioxane (600 ml) and 1-(3'-diethylaminopropoxy)-2,4-diaminobenzene trihydrochloride (47.2 g) was added dropwise 2-methoxybenzoylchloride (73 g) while stirring at 5°–10° C in an atomosphere of nitrogen followed by stirring the mixture at that temperature for 30 minutes. After continuing the stirring at room temperature for 2 hours, water (3 l) was added to the mixture which was extracted with benzene. The benzene layer was washed with water, dried, and condensed to dryness. The residue was recrystallized from methanol-water and then recrystallized again from benzene-hexane to obtain 46 g of 1-(3'-diethylaminopropoxy)-2,4-bis(2"-methoxybenzamido)-benzene having a melting point between 114°–115° C.

Analysis: Calcd. for $C_{29}H_{35}N_3O_5$: C, 68.9; H, 7.0; N, 8.3 (%) Found: C, 69.3; H, 7.1; N, 8.4 (%).

EXAMPLE 25

To a mixture of potassium carbonate (12.4 g), sodium acetate trihydrate (37 g), water (240 ml) and dioxane (240 ml) was added N-)2,4-diaminophenyl)-N'-methylpiperazine trihydrochloride (19 g) at 5°–10° C, immediately followed by the addition of 2-methoxybenzoylchloride (31 g). The mixture was stirred at 5°–10° C for 30 minutes and then at room temperature for 30 minutes. To the mixture was added water (1l) followed by the addition of potassium carbonate (30 g) and the mixture was allowed to stand overnight to precipitate crystals. The crystals were recovered by filtration, washed with water, dried and recrystallized from ethyl acetate to obtain 20 g of N-[2,4-bis(2'-methoxybenzamido)-phenyl]-N'-methylpiperazine having a melting point between 177°–178° C.

Analysis: Calcd. for $C_{27}H_{30}N_4O_4$: C, 68.3; H, 6.4; N, 11.8 (%) Found: C, 68.2; H, 6.4; N, 11.9 (%).

EXAMPLE 26

By a procedure similar to that described in Example 21, 1-(2'-diethylaminoethoxy)-2,4-diaminobenzene trihydrochloride and 2-methoxybenzoylchloride were subjected to condensation reaction. The product as it was, in the form of free base, was recrystallized from benzene to obtain 1-(2'-diethylaminoethoxy)-2,4-bis(2"-methoxybenzamido)-benzene having a melting point between 143°–144° C. (Yield: 69%)

Analysis: Calcd. for $C_{28}H_{33}N_3O_5$: C, 68.4; H, 6.8; N, 8.6 (%) Found: C, 68.7; H, 6.9; N, 8.6 (%).

EXAMPLE 27

By a procedure similar to that described in Example 21, 1-(2'-dimethylaminoethoxy)-2,4-diaminobenzene trihydrochloride and 2-methoxybenzoylchloride were subjected to condensation reaction. The product was extracted with benzene and the basic substance was transferred from the benzene layer to an aqueous layer with the use of diluted hydrochloric acid. If the hydrochloric acid addition salt of the substance did not dissolve, a small amount of methanol was used. The aqueous layer was washed with benzene and, after adjusting its pH to between 9–10 by the addition of potassium carbonate, extracted again with benzene. The extract was washed with water, dried over potassium carbonate and condensed to dryness. The residue was purified by silica gel column chromatography eluting with benzenemethanol and was recrystallized from methanol to obtain 1-(2'-dimethylaminoethoxy)-2,4-bis(2"-methoxybenzamido)benzene having a melting point between 149°–150° C. (Yield: 62%)

Analysis: Calcd. for $C_{26}H_{29}N_3O_5$: C, 67.4; H, 6.3; N, 9.1 (%) Found: C, 67.3; H, 6.3; N, 9.1 (%).

EXAMPLE 28

To a mixture of potassium carbonate (5 g), water (30 ml) and dioxane (30 ml) were added 1-(2'-diethylaminoethyl)-2,4-diaminobenzene trihydrochloride (3.9 g) and 2-ethoxybenzoylchloride (5.4 g) at 5°–10° C followed by stirring at that temperature for 1 hour. Water (200 ml) was added to the mixture and, after adjusting its pH to between 9–10, the mixture was extracted with benzene. The benzene layer was washed with water and dried, gaseous hydrogen chloride was bubbled into the benzene layer to precipitate crystals of hydrochloric acid addition salt which were recrystallized from isopropanol. The crystals were dissolved in water and, after the addition of potassium carbonate, extracted with benzene. The extract was condensed to dryness and the residue was recrystallized from tetrahydrofuran-diethylether-hexane to obtain 4.0 g of 1-(2'-diethylaminoethyl)-2,4-bis(2"-ethoxybenzamido)-benzene having a melting point between 91°–92° C.

Analysis: Calcd. for $C_{30}H_{37}N_3O_4$: C, 71.5; H, 7.4; N, 8.3 (%) Found: C, 71.7; H, 7.5; N, 8.1 (%).

EXAMPLE 29

To a mixture of potassium carbonate (3.5 g), sodium acetate trihydrate (11 g), water (50 ml) and tetrahydrofuran (60 ml) were added 1-(2'-dimethylaminoethyl)-2,4-diaminobenzene trihydrochloride (5 g) and 2-acetoxybenzoylchloride (11 g) at 0°–5° C followed by stirring at 5°–10° C for 1 hour. After the addition of concentrated aqueous ammonia (40 ml), the reaction mixture was allowed to stand at room temperature for 30 minutes. Water (500 ml) was added to the mixture and its pH was adjusted to between 7–8. Undissolved substances were recovered, washed with water, dried and dissolved in benzene. Gaseous hydrogen chloride was bubbled into the benzene solution to precipitate crystals of hydrochloric acid addition salt. Recrystallization of the crystals from isopropanol gave 4.8 g of 1-(2'-dimethylaminoethyl)-2,4-bis(2"-hydroxybenzamido)-benzene hydrochloride having a melting point between 245°–247° C (decomposition).

Analysis: Calcd. for $C_{24}H_{26}N_3O_4Cl$: C, 63.2; H, 5.7; N, 9.2 (%) Found: C, 63.2; H, 5.7; N, 8.9 (%).

EXAMPLE 30

To a mixture of potassium carbonate (22 g), water (80 ml) and dioxane (90 ml) was added at 5°–10° C 1-[N-(2'-diethylaminoethyl)-carbamoyl]-2,4-diaminobenzene trihydrochloride (11 g). Then, 2-methoxybenzoylchloride (11.2 g) was added dropwise to the mixture in an atmosphere of nitrogen over 30 minutes followed by stirring at room temperature for 1 hour. Water (500 ml) was added to the reaction mixture and the mixture was extracted with benzene. The extract was washed with water and dried and gaseous hydrogen chloride was bubbled into it to precipitate crystals as hydrochloric acid addition salt. The crystals were recrystallized from ethanol to obtain 11 g of 1-[N-(2'-diethylaminoethyl)-carbamoyl]-2,4-bis(2''-methoxybenzamido)-benzene hydrochloride having a melting point between 181°–182° C.

Analysis: Calcd. for $C_{29}H_{35}N_4O_5Cl$: C, 62.7; H, 6.4; N, 10.1 (%) Found: C, 62.5; H, 6.4; N, 10.0 (%).

EXAMPLE 31

By a procedure similar to that described in Example 30, 1-[N-(2'-diethylaminoethyl)-carbamoyl]-3,5-diaminobenzene trihydrochloride and 2-methoxybenzoylchloride were subjected to condensation reaction and the reaction mixture was treated to obtain crystals as hydrochloric acid addition salt. Recrystallization of the crystals from isopropanol gave 1-[N-(2'-diethylaminoethyl)-carbamoyl]-3,5-bis(2''-methoxybenzamido)-benzene hydrochloride having a melting point between 187°–189° C. (Yield: 72%)

Analysis: Calcd. for $C_{29}H_{35}N_4O_5Cl$: C, 62.7; H, 6.4; N, 10.1 (%) Found: C, 62.9; H, 6.3; N, 10.0 (%).

EXAMPLE 32

By a procedure similar to that described in Example 29, 1-(2'-diethylaminoethyl)-2,4-diaminobenzene trihydrochloride and 2-acetoxybenzoylchloride were subjected to condensation reaction and the product was treated to obtain 1-(2'-diethylaminoethyl)-2,4-bis(2''-hydroxybenzamido)-benzene hydrochloride having a melting point between 246°–248° C (decomposition). (Yield: 49%)

Analysis: Calcd. for $C_{26}H_{30}N_3O_4Cl$: C, 64.5; H, 6.2; N, 8.7 (%) Found: C, 64.3; H, 6.0; N, 8.9 (%).

EXAMPLE 33

Crude 1-(2'-diethylaminoethoxy)-2,4-bis(2''-hydroxybenzamido)-benzene as free base (3 g) obtained according to Example 22 was dissolved in acetic anhydride (20 ml). After allowing the solution to stand overnight, gaseous hydrogen chloride was bubbled into the solution to obtain the corresponding hydrochloride and condensed under reduced pressure to dryness. The residue was recrystallized from acetone to obtain 2.1 g of 1-(2'-diethylaminoethoxy)-2,4-bis(2''-acetoxybenzamido)-benzene hydrochloride having a melting point between 168°–170° C.

Analysis: Calcd. for $C_{30}H_{34}N_3O_7Cl$: C, 61.7; H, 5.9; N, 7.2 (%) Found: C, 61.8; H, 6.2; N, 7.0 (%).

EXAMPLE 34

By a procedure similar to that described in Example 33, crude N-[2,4-bis(2'-hydroxybenzamido)-phenyl]-N-methylpiperazine as free base (1 g) obtained according to Example 23 treated to obtain a crystalline product. The crystals were recrystallized from isopropanol to obtain 0.5 g of N-[2,4-bis(2'-acetoxybenzamido)-phenyl]-N'-methylpiperazine hydrochloride having a melting point between 228°–230° C (decomposition).

Analysis: Calcd. for $C_{29}H_{31}N_4O_6Cl$: C, 61.4; H, 5.5; N, 9.9 (%) Found: C, 61.0; H, 5.5, N, 9.7 (%).

EXAMPLE 35

By a procedure similar to that described in Example 21, 1-(2'-diethylaminoethyl)-2,4-diaminobenzene trihydrochloride and 2-methoxybenzoylchloride were subjected to condensation reaction. After the completion of the reaction, the mixture was extracted with benzene and the benzene layer was washed with water and dried. Gaseous hydrogen chloride was bubbled into the benzene layer to precipitate crystals as the corresponding hydrochloric acid addition salt. The crystals were recovered by filtration and recrystallized from isopropanol to obtain 1-(2'-diethylaminoethyl)-2,4-bis(2''-methoxybenzamido)-benzene hydrochloride having a melting point between 188°–189° C. (Yield: 64%)

Analysis: Calcd. for $C_{28}H_{34}N_3O_4Cl$: C, 65.7; H, 6.7; N, 8.2 (%) Found: C, 65.4; H, 6.7; N, 8.0 (%).

EXAMPLE 36

By a procedure similar to that described in Example 30, 1-[N-(3'-diethylaminopropyl)-carbamoyl]-2,4-diaminobenzene trihydrochloride and 2-methoxybenzoylchloride were subjected to condensation reaction and then the reaction mixture was treated in a manner similar to that in Example 30 to obtain the corresponding hydrochloric acid addition salt. The salt was recrystallized from isopropanol, converted to its free base and then recrystallized from benzene-diethylether to obtain 1-[N-(3'-diethylaminopropyl)-carbamoyl]-2,4-bis(2''-methoxybenzamido)-benzene having a melting point between 107°–108° C. (Yield: 67%)

Analysis:

Calcd. for $C_{30}H_{36}N_4O_5$: C, 67.6; H, 6.8; N, 10.5 (%) Found: C, 67.8; H, 6.8; N, 10.5 (%).

EXAMPLE 37

By a procedure similar to that described in Example 27, 1-(3'-dimethylaminopropoxy)-2,4-diaminobenzene trichloride and 2-methoxybenzoylchloride were subjected to condensation reaction and the reaction mixture was treated in a manner similar to that in Example 27 to obtain hydrochloric acid addition salt. Recrystallization of the salt from isopropanol gave 1-(3'-dimethylaminopropoxy)-2,4-bis(2''-methoxybenzamido)-benzene trihydrochloride having a melting point between 180°–181° C. (Yield: 68%)

Analysis: Calcd. for $C_{27}H_{32}N_3O_5Cl$: C, 63.1; H, 6.3; N, 8.2 (%) Found: C, 62.9; H, 6.3; N, 8.3 (%).

EXAMPLE 38

By a procedure similar to that described in Example 27, 1-(2'-dimethylamino-2',2'-dimethylethoxy)-2,4-diaminobenzene trihydrochloride and 2-methoxybenzoylchloride were subjected to condensation reaction and the reaction product in the form of free base was purified by silica gel column chromatography (eluent:

CHCl$_3$:methanol = 10:1) to obtain 1-(2'-dimethylamino-2',2'-dimethylethoxy)-2,4-bis(2''-methoxybenzamido)-benzene as colorless amorphous powder. (Yield: 52%)

Analysis: Calcd. for C$_{28}$H$_{33}$N$_3$O$_5$: C, 68.4; H, 6.8; N, 8.6 (%) Found: C, 68.3; H, 7.1; N, 8.5 (%).

I. R. Spectrum (KBr disc) (cm$^{-1}$): 3330, 2900, 1660, 1590, 1540, 1480, 1300, 1020, 750.

N.M.R. Spectrum (CDCl$_3$ solution; δ): 3.98 (6H, s), 3.87 (2H, s), 2.20 (6H, s), 1.12 (6H, s).

EXAMPLE 39

By a procedure similar to that described in Example 27, 2,4-diamino-N-methyl-N-(2'-dimethylaminoethyl)-aniline trihydrochloride and 2-methoxybenzoylchloride were subjected to condensation reaction and the product in the form of free base was purified by silica gel column chromatography (eluent: CHCl$_3$:methanol = 10:1) to obtain 2,4-bis(2'-methoxybenzamido)-N-methyl-N-(2''-dimethylaminoethyl)-aniline as colorless amorphous powder. (Yield: 51%)

Analysis: Calcd. for C$_{27}$H$_{32}$N$_4$O$_4$: C, 68.0; H, 6.8; N, 11.8 (%) Found: C, 68.0; H, 6.9; N, 11.5 (%).

I. R. Spectrum (KBr disc) (cm$^{-1}$): 3340, 3270, 2900, 1660, 1600, 1540, 1470, 1290, 1020, 750.

N.M.R. Spectrum (CDCl$_3$ solution: δ): 3.98 (6H, s), 3.09 (2H, t, J=9Hz), 2.69 (3H, s), 2.30 (2H, t, J=9Hz), 2.07 (6H, s).

EXAMPLE 40

By a procedure similar to that described in Example 35, 1-[2'-(N-morpholino)-ethyl]-2,4-diaminobenzene trihydrochloride and 2-methoxybenzoylchloride were subjected to condensation reaction and the reaction mixture was treated in a manner similar to that in Example 35 to obtain 1-[2'-(N-morpholino)-ethyl]-2,4-bis(2''-methoxybenzamido)-benzene hydrochloride having a melting point between 220°-221° C. (Yield: 59%)

Analysis: Calcd. for C$_{28}$H$_{32}$N$_3$O$_5$Cl: C, 63.9; H, 6.1; N, 8.0 (%) Found: C, 63.7; H, 6.0; N, 7.9 (%).

EXAMPLE 41

By a procedure similar to that described in Example 35, 1-[2'-(N-piperidino)-ethyl]-2,4-diaminobenzene trihydrochloride and 2-methoxybenzoylchloride were subjected to condensation reaction and the reaction mixture was treated in a manner similar to that in Example 35 to recover the product as hydrochloric acid addition salt. The salt was recrystallized from isopropanol, converted to the corresponding free base and then recrystallized again from benzene-diethylether to obtain 1-[2'-(N-piperidino)-ethyl]-2,4-bis(2''-methoxybenzamido)-benzene having a melting point between 127°-128° C (Yield: 60%).

Analysis: Calcd. for C$_{29}$H$_{33}$N$_3$O$_4$: C, 71.4; H, 6.8; N, 8.6 (%) Found: C, 71.3; H, 6.9; N, 8.8 (%).

EXAMPLE 42

By a procedure similar to that described in Example 30, 1-[N-(2'-diethylaminoethyl)-carbamoyl]-2,5-diaminobenzene trihydrochloride and 2-methoxybenzoylchloride were subjected to condensation reaction and the reaction mixture was treated in a manner similar to that in Example 30 to obtain 1-[N-(2'-diethylaminoethyl)-carbamoyl]-2,5-bis(2'''-methoxybenzamido)-benzene hydrochloride having a melting point between 213°-214° C (decomposition). (Yield: 67%)

Analysis: Calcd. for C$_{29}$H$_{35}$N$_4$O$_5$Cl: C, 62.7; H, 6.4; N, 10.1 (%) Found: C, 62.6; H, 6.2; N, 9.8 (%).

EXAMPLE 43

By a procedure similar to that described in Example 13, 1-[N-(3'-dimethylaminopropyl)-carbamoyl]-2,4-diaminobenzene trihydrochloride and 2-methylbenzoylchloride were subjected to condensation reaction and the reaction mixture was treated in a manner similar to that in Example 13 to obtain 1-[N-(3'-dimethylaminopropyl)-carbamoyl]-2,4-bis(2''-methylbenzamido)-benzene having a melting point between 164°-165° C. (Yield: 68%)

Analysis: Calcd. for C$_{28}$H$_{32}$N$_3$O$_4$: C, 71.2; H, 6.8; N, 11.9 (%) Found: C, 70.9; H, 6.9; N, 11.7 (%).

EXAMPLE 44

By a procedure similar to that described in Example 13, 1-[N-(3'-dimethylaminopropyl)-carbamoyl]-2,4-diaminobenzene trihydrochloride and 4-methylbenzoylchloride were subjected to condensation reaction and the reaction mixture was treated in a manner similar to that in Example 13 to obtain 1-[N-(3'-dimethylaminopropyl)-carbamoyl]-2,4-bis(4''-methylbenzamido)-benzene having a melting point between 195°-196° C. (Yield: 63%)

Analysis: Calcd. for C$_{28}$H$_{32}$N$_3$O$_4$: C, 71.2; H, 6.8; N, 11.9 (%) Found: C, 71.1; H, 6.7; N, 11.9 (%).

EXAMPLE 45

By a procedure similar to that described in Example 13, 1-[N-(3'-dimethylaminopropyl)-carbamoyl]-2,4-diaminobenzene trihydrochloride and 3-methylbenzoylchloride were subjected to condensation reaction and the reaction mixture was treated in a manner similar to that in Example 13 to obtain 1-[N-(3'-dimethylaminopropyl)-carbamoyl]-2,4-bis(3''-methylbenzamido)-benzene having a melting point between 172° – 173° C. (Yield: 71%)

Analysis:
Calcd. for C$_{28}$H$_{32}$N$_3$O$_4$: C, 71.2; H, 6.8; N, 11.9 (%)
Found: C, 71.3 H, 6.7; N, 11.7 (%).

EXAMPLE 46

By a procedure similar to that described in Example 13, 1-[N-(3'-dimethylaminopropyl)-carbamoyl]-2,4-diaminobenzene trihydrochloride and 2-methoxy-4-methylbenzoylchloride were subjected to condensation reaction and the reaction mixture was treated in a manner similar to that in Example 13 to obtain 1-[N-(3'-dimethylaminopropyl)-carbamoyl]-2,4-bis(2''-methoxy-4''-methylbenzamido)-benzene having a melting point between 127° – 129° C. (Yield: 60%)

Analysis: Calcd. for C$_{30}$H$_{36}$N$_4$O$_5$: C, 67.7; H, 6.8; N, 10.5 (%) Found: C, 67.5; H, 6.9; N, 10.4 (%)

EXAMPLE 47

By a procedure similar to that described in Example 13, 1-[N-(3'-dimethylaminopropyl)-carbamoyl]-2,4-diaminobenzene trihydrochloride and benzoylchloride were subjected to condensation reaction and the reaction mixture was treated in a manner similar to that in Example 13 to obtain 1-[N-(3'-dimethylaminopropyl)-carbamoyl]-2,4-bis(benzamido)-benzene having a melting point between 196° – 197° C. (Yield: 66%)

Analysis: Calcd. for C$_{26}$H$_{28}$N$_4$O$_3$: C, 70.3; H, 6.4; N, 12.6 (%) Found: C, 70.2; H, 6.4; N, 12.5 (%).

EXAMPLE 48

By a procedure similar to that described in Example 6, 1-(2'-diethylaminoethoxy)-2,4-diaminobenzene trihydrochloride and 2-ethoxybenzoylchloride were subjected to condensation reaction and the reaction mixture was treated in a manner similar to that in Example 6 to obtain 1-(2'-diethylaminoethoxy)-2,4-bis(2''-ethoxybenzamido)-benzene having a melting point between 194° – 195° C. (Yield: 55%)

Analysis: Calcd. for $C_{30}H_{38}N_3O_5Cl$: C, 64.8, H, 6.9, N, 7.6 (%) Found: C, 65.0, H, 6.8, N, 7.6 (%).

EXAMPLE 49

By a procedure similar to that described in Example 6, 1-[3'-(N-piperidino)-propoxy]-2,4-diaminobenzene trihydrochloride and 2-methylbenzoylchloride were subjected to condensation reaction and the reaction mixture was treated in a manner similar to that in Example 6 to obtain 1-[3'-(N-piperidino)-propoxy]-2,4-bis(2''-methylbenzamido)-benzene having a melting point between 77° – 79° C. (Yield: 65%)

Analysis: Calcd. for $C_{29}H_{35}N_3O_3$: C, 73.5, H, 7.5, N, 8.9 (%) Found: C, 73.6, H, 7.4, N, 8.7 (%).

What is claimed is:

1. A bis(benzamido)-benzene derivative represented by the formula

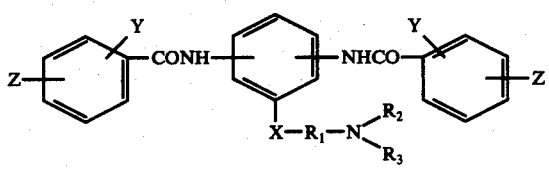

wherein X is direct bond, oxygen,

or —CONH— wherein the CO moiety is bonded to the phenylene group, $R_1$ is straight or branched lower alkylene, $R_2$ and $R_3$ are the same or different and each represents lower alkyl or they may be bonded to each other directly or through a hetero atom to form piperidino or morpholino, $R_4$ is lower alkyl and it may be bonded to $R_2 R_3$ to form piperazino and Y and Z are same or different and each represents hydrogen, lower alkyl, hydroxy, lower alkoxy, lower alkanoyloxy or halogen, and its acid addition salt.

2. A bis(benzamido)-benzene derivative represented by the formula

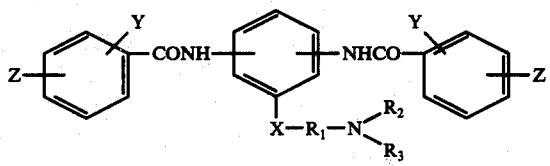

wherein X is oxygen or —CONH— wherein the CO moiety is bonded to the phenylene group, Y and Z are the same or different and each represents methyl, methoxy, ethoxy, hydroxy, acetoxy, chlorine or hydrogen, $R_1$ is ethylene, propylene or butylene, $R_2$ and $R_3$ are the same or different and each represents methyl or ethyl or they may be bonded to each other directly or through a hetero atom to form piperidino or morpholino, and its acid addition salt.

3. A bis(benzamido)-benzene derivative represented by the formula

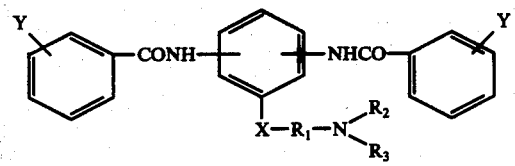

wherein X is oxygen or —COHN— wherein the CO moiety is bonded to the phenylene group, Y is methyl or methoxy, $R_1$ is ethylene or propylene, and $R_2$ and $R_3$ are independently methyl or ethyl, and its acid addition salt.

4. A bis(benzamido)-benzene derivative represented by the formula

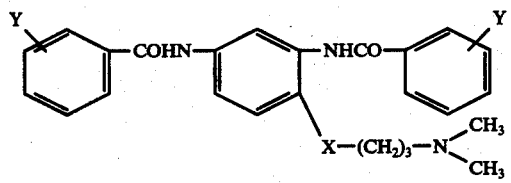

wherein X is oxygen or —CONH— wherein the CO moiety is bonded to the phenylene group, and Y is methyl attached to o- or m-position of the benzene, and its acid addition salt.

5. 1-(3'-Diethylaminopropoxy)-2,4-bis(2''-methylbenzamido)-benzene according to claim 2.

6. 1-(3'-Diethylaminopropoxy)-2,4-bis(3''-methylbenzamido)-benzene according to claim 2.

7. 1-[N-(2'-diethylaminoethyl)-carbamoyl]-2,4-bis(2''-methylbenzamido)-benzene according to claim 2.

8. 1-(3'-Diethylaminopropoxy)-2,4-bis(4''-methylbenzamido)-benzene according to claim 2.

9. 1-(3'-Diethylaminopropoxy)-2,4-bis(benzamido)-benzene according to claim 2.

10. 1-(3'-Dimethylaminopropoxy)-2,4-bis(2''-methylbenzamido)-benzene according to claim 2.

11. 1-(3'-Dimethylaminopropoxy)-2,4-bis(3''-methylbenzamido)-benzene according to claim 2.

12. 1-(3'-Dimethylaminopropoxy)-2,4-bis(4''-methylbenzamido)-benzene according to claim 2.

13. 1-(3'-Diethylaminopropoxy)-2,4-bis(2''-methoxy-4''-methylbenzamido)-benzene according to claim 2.

14. 1-(3'-Dimethylaminopropoxy)-2,4-bis(2'',3''-dimethoxybenzamido)-benzene according to claim 2.

15. 1-(3'-Diethylaminopropoxy)-2,4-bis(2''-chlorobenzamido)-benzene according to claim 2.

16. 1-(3'-Diethylaminopropoxy)-2,4-bis(4'''-methoxybenzamido)-benzene according to claim 2.

17. 1-[N-(3'-diethylaminopropyl)-carbamoyl]-2,4bis(2''-methylbenzamido)-benzene according to claim 2.

18. 1-(4'-Dimethylaminobutoxy)-2,4-bis(2''-methylbenzamido)-benzene according to claim 2.

19. 1-(4'-Dimethylaminobutoxy)-2,4-bis(3''-methylbenzamido)-benzene according to claim 2.

20. 1-[N-(2'-diethylaminoethyl)-carbamoyl]-2,4-bis(3''-methylbenzamido)-benzene according to claim 2.

21. 1-[2'-(N-morpholino)-ethoxy]-2,4-bis(2''-methylbenzamido)-benzene according to claim 2.

22. 1-[N-(3'-diethylaminopropyl)-carbamoyl]-2,4-bis(3"-methylbenzamido)-benzene according to claim 2.

23. 1-[N-(2'-diethylaminoethyl)-carbamoyl]-2,4-bis(4"-methylbenzamido)-benzene according to claim 2.

24. 1-(3'-Dimethylaminopropoxy)-2,4-bis(4"-methoxybenzamido)-benzene according to claim 2.

25. 1-(2'-Diethylaminoethoxy)-2,4-bis(2"-ethoxybenzamido)-benzene according to claim 2.

26. 1-(2'-Diethylaminoethoxy)-2,4-bis(2"-hydroxybenzamido)-benzene according to claim 2.

27. N-[2,4-bis(2"-hydroxybenzamido)-phenyl]-N'-methylpiperazne according to claim 1.

28. 1-(3'-Diethylaminopropoxy)-2,4-bis(2"-methoxybenzamido)-benzene according to claim 2.

29. N-[2,4-bis(2"-methoxybenzamido)-phenyl]-N'-methylpiperazine according to claim 2.

30. 1-(2'-Diethylaminoethoxy)-2,4-bis(2"-methoxybenzamido)-benzene according to claim 2.

31. 1-(2'-Dimethylaminoethoxy)-2,4-bis(2"-methoxybenzamido)-benzene according to claim 2.

32. 1-(2'-Diethylaminoethoxy)-2,4-bis(2"-ethoxybenzamido)-benzene according to claim 1.

33. 1-(2'-Dimethylaminoethyl)-2,4-bis(2"-hydroxybenzamido)-benzene according to claim 1.

34. 1-[N-(2'-diethylaminoethyl)-carbamoyl]-2,4-bis(2"-methoxybenzamido)-benzene according to claim 2.

35. 1-[N-(2'-diethylaminoethyl)-carbamoyl]-3,5-bis(2"-methoxybenzamido)-benzene according to claim 2.

36. 1-(2'-Diethylaminoethyl)-2,4-bis(2"-hydroxybenzamido)-benzene according to claim 1.

37. 1-(2'-Diethylaminoethoxy)-2,4-bis(2"-acetoxybenzamido)-benzene according to claim 2.

38. N-[2,4-bis(2'-acetoxybenzamido)-phenyl]-N'-methylpiperazine according to claim 1.

39. 1-(2'-Diethylaminoethyl)-2,4-bis(2"-methoxybenzamido)-benzene according to claim 1.

40. 1-[N-(3'-diethylaminopropyl)-carbamoyl]-2,4-bis(2"-methoxybenzamido)-benzene according to claim 2.

41. 1-(3'-Dimethylaminopropoxy)-2,4-bis(2"-methoxybenzamido)-benzene according to claim 2.

42. 1-(2'-Dimethylamino-2',2'-dimethylethoxy)-2,4-bis(2"-methoxybenzamido)-benzene according to claim 2.

43. 2,4-Bis(2"-methoxybenzamido)-N-methyl-N-(2"-dimethylaminoethyl)-aniline according to claim 1.

44. 1-[2'-(N-morpholino)-ethyl]-2,4-bis(2"-methoxybenzamido)-benzene according to claim 1.

45. 1-[2'-(N-piperidino)-ethyl]-2,4-bis(2"-methoxybenzamido)-benzene according to claim 1.

46. 1-[N-(2'-diethylaminoethyl)-carbamoyl]-2,5-bis(2"-methoxybenzamido)-benzene according to claim 2.

47. 1-[N-(3'-dimethylaminopropyl)-carbamoyl]-2,4-bis(2"-methylbenzamido)-benzene according to claim 2.

48. 1-[N-(3'-dimethylaminopropyl)-carbamoyl]-2,4-bis(4"-methylbenzamido)-benzene according to claim 2.

49. 1-[N-(3'-dimethylaminopropyl)-carbamoyl]-2,4-bis(3"-methylbenzamido)-benzene according to claim 2.

50. 1-[N-(3'-dimethylaminopropyl)-carbamoyl]-2,4-bis(2"-methoxy-4"-methylbenzamido)-benzene according to claim 2.

51. 1-[N-(3'-dimethylaminopropyl)-carbamoyl]-2,4-bis(benzamido)-benzene according to claim 2.

52. 1-(2'-Diethylaminoethoxy)-2,4-bis(2"-ethoxybenzamido)-benzene according to claim 2.

53. 1-[3'-(N-piperidino)-propoxy]-2,4-bis(2"-methylbenzamido)-benzene according to claim 2.

54. A bis(benzamido)-benzene derivative in accordance with claim 1, wherein X is direct bond, oxygen or

wherein $R_4$ is lower alkyl, $R_1$ is straight or branched lower alkylene, $R_2$ and $R_3$ are the same or different and each represents lower alkyl and Y and Z are the same or different and each represents hydrogen, lower alkyl, lower alkoxy, or halogen.

* * * * *

UNITED STATES PATENT AND TRADEMARK OFFICE
CERTIFICATE OF CORRECTION

PATENT NO. : 4,058,523
DATED : November 15, 1977
INVENTOR(S) : MORI et al.

It is certified that error appears in the above-identified patent and that said Letters Patent are hereby corrected as shown below:

Column 2, line 44, "-COHN" should read -- -CONH- --

Column 2, line 64, "compound" should read --compound (IV). --

Column 4, line 28, "(N'-piperidino)" should read --(N'-piperizino)--

Column 21, line 50, "drozy" should read --droxy--

Column 22, line 59, "2,4bis" should read --2,4-bis--

Column 23, line 17, "Claim 2" should read --Claim 1--

Signed and Sealed this

Twenty-fifth Day of July 1978

[SEAL]

Attest:

RUTH C. MASON
Attesting Officer

DONALD W. BANNER
Commissioner of Patents and Trademarks